United States Patent
Abbasi et al.

(10) Patent No.: US 8,145,326 B2
(45) Date of Patent: Mar. 27, 2012

(54) INTRA-COCHLEAR ELECTRODE WITH A PARTIALLY DETACHABLE HYDROPHILIC SEGMENT FOR DEFERRED SELF-POSITIONING

(75) Inventors: Farhang Abbasi, East Azerbayjan (IR); Claude Jolly, Voels (AT); Mohammad Farhadi, Tehran (IR); Erwin S. Hochmair, Axams (AT); Hamid Mirzadeh, Tehran (IR)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 231 days.

(21) Appl. No.: 11/934,962

(22) Filed: Nov. 5, 2007

(65) Prior Publication Data

US 2008/0058914 A1 Mar. 6, 2008

Related U.S. Application Data

(62) Division of application No. 10/243,633, filed on Sep. 13, 2002, now abandoned.

(60) Provisional application No. 60/322,049, filed on Sep. 13, 2001.

(51) Int. Cl.
*A61N 1/04* (2006.01)
(52) U.S. Cl. .............................. 607/137; 607/2
(58) Field of Classification Search .............. 607/2, 137; 525/477

See application file for complete search history.

(56) References Cited

U.S. PATENT DOCUMENTS

| | | | | |
|---|---|---|---|---|
| 4,364,813 A * | 12/1982 | White | ..................... | 204/252 |
| 4,445,985 A * | 5/1984 | Korach | ..................... | 205/433 |
| 4,898,183 A | 2/1990 | Kuzma | | |
| 5,232,984 A * | 8/1993 | Hubbell et al. | .............. | 525/54.1 |
| 5,397,848 A * | 3/1995 | Yang et al. | ..................... | 525/477 |
| 5,545,219 A * | 8/1996 | Kuzma | .............................. | 623/10 |
| 5,578,084 A * | 11/1996 | Kuzma et al. | ..................... | 623/10 |
| 5,653,742 A | 8/1997 | Parker et al. | | |
| 5,876,443 A | 3/1999 | Hochmair et al. | | |
| 5,999,859 A | 12/1999 | Jolly | | |
| 6,078,841 A | 6/2000 | Kuzma | | |
| 6,231,604 B1 | 5/2001 | von Ilberg | | |
| 6,377,849 B1 | 4/2002 | Lenarz et al. | | |
| 6,421,569 B1 | 7/2002 | Treaba et al. | | |
| 6,556,870 B2 | 4/2003 | Zierhofer et al. | | |
| 2002/0082554 A1 | 6/2002 | Lenarz et al. | | |
| 2002/0111664 A1* | 8/2002 | Bartig et al. | .................. | 607/122 |
| 2006/0095045 A1* | 5/2006 | Trieu | .............................. | 606/99 |

FOREIGN PATENT DOCUMENTS

WO 9306698 A1 4/1993

OTHER PUBLICATIONS

International Search Report dated Feb. 7, 2003.

* cited by examiner

*Primary Examiner* — Carl H Layno
*Assistant Examiner* — Pamela M Bays
(74) *Attorney, Agent, or Firm* — Sunstein Kann Murphy & Timbers LLP

(57) ABSTRACT

A perimodiolar electrode for cochlear implantation includes an electrode carrier having a front end and a back end. The electrode carrier includes one or more contacts and a hydrophilic segment that swells after insertion in a cochlea and detaches at least in part from the carrier. In accordance with related embodiments, the hydrophilic segment may detach from the electrode carrier between the front end and the back end. The detached hydrophilic segment may surround the modiolus of a scala tympani of the cochlea or the inner wall of a scala tympani of the cochlea.

11 Claims, 5 Drawing Sheets

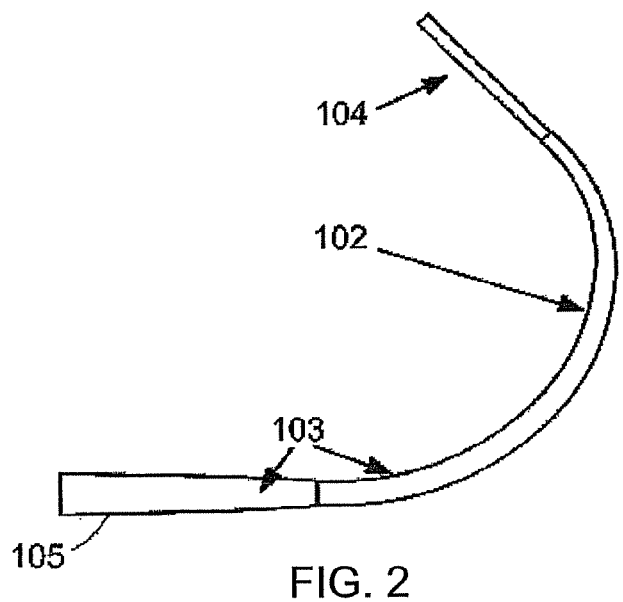
FIG. 2
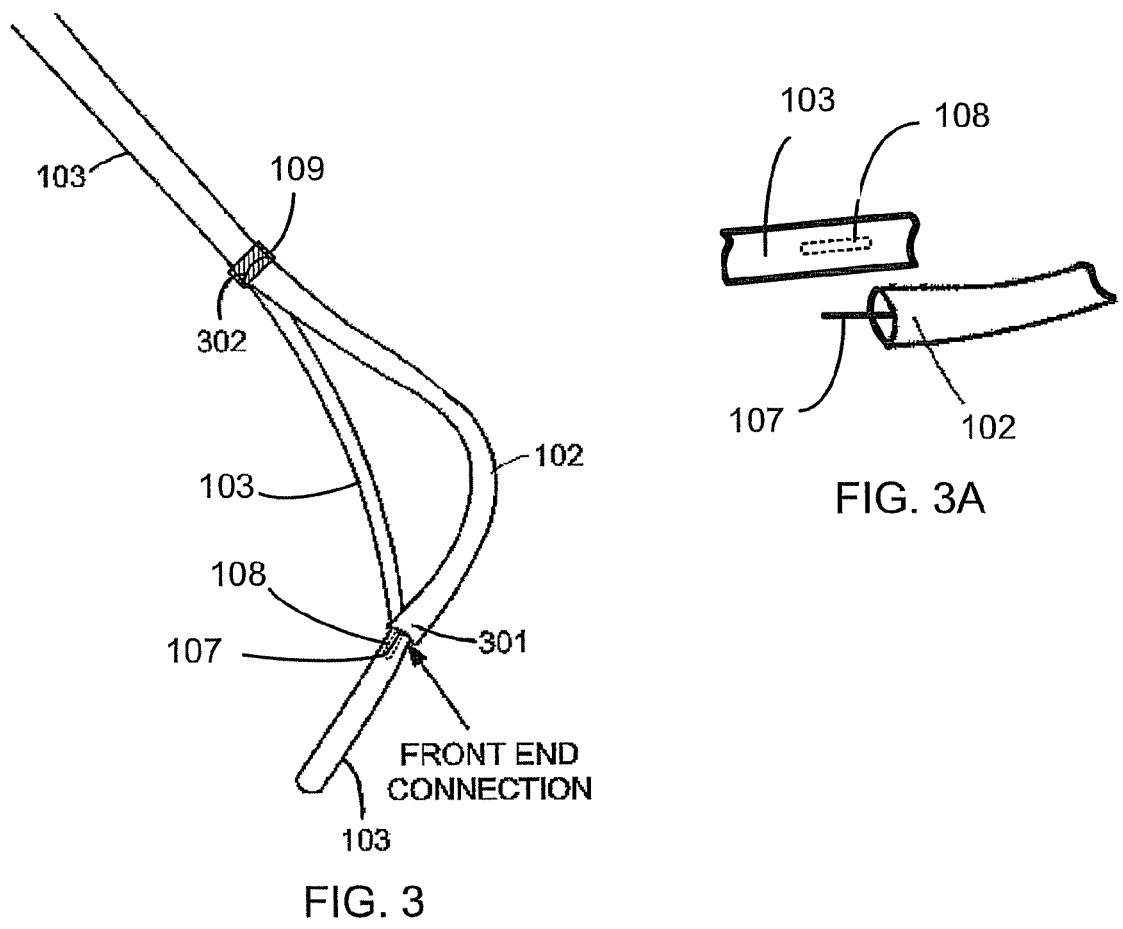
FIG. 3A
FIG. 3

INTRA-COCHLEAR ELECTRODE WITH A PARTIALLY DETACHABLE HYDROPHILIC SEGMENT FOR DEFERRED SELF-POSITIONING

CROSS-REFERENCE TO RELATED APPLICATIONS

The present application is a divisional of application Ser. No. 10/243,633, filed Sep. 13, 2002, which claims priority from U.S. Provisional Patent Application No. 60/322,049, filed Sep. 13, 2001, the disclosures of which are hereby incorporated herein, in their entirety, by reference.

TECHNICAL FIELD

The present invention relates to cochlear implants, and more particularly to a perimodiolar electrode designed for cochlear implantation.

BACKGROUND

It is known to provide implants containing electrodes for stimulation of nerve tissue. Such implants include, for example, pacemakers, oral implants for stimulating muscle tissue in the mouth of a subject or patient as well as nerve tissue associated with a subject's sinus cavity and cochlear implants for stimulating the tissues of the inner ear. In the case of cochlear implants, the dynamic range of stimulation is often limited and channel interaction often interferes with the effectiveness of the implant. Channel interaction may be caused by the temporal integration of charges at the membrane level or by the field overlap from individual electrodes.

Another problem associated with cochlear implants, is a tendency for the electrode to move after placement in the ear. Such movement decreases the control of place stimulation, and consequently lowers the hearing performance of the subject. Movement of the electrode of a cochlear implant may also contribute to unwanted and unnecessary nerve stimulation such as facial nerve stimulation.

Recently, polydimethylsiloxane (PDMS)-based elastomers have been used in a wide range of biomedical applications. Due to their physiological inertness, good blood compatibility, low toxicity, good thermal and oxidative stability, low modulus and anti-adhesive properties. There has been an increasing interest in silicone rubber/hydrogels multi-component systems for various biomedical applications.

SUMMARY

In accordance with a first embodiment of the invention, a perimodiolar electrode for cochlear implantation includes an electrode carrier having a front end and a back end. The carrier includes one or more contacts and a hydrophilic segment that swells after insertion in a cochlea and detaches at least in part from the carrier. In accordance with related embodiments, the hydrophilic segment may detach from the electrode carrier between the front end and the back end. The detached hydrophilic segment may surround the modiolus of a scala tympani of the cochlea or the inner wall of a scala tympani of the cochlea. In accordance with further related embodiments, the electrode carrier may include an elastomer. Similarly, the hydrophilic segment may include an elastomer and a metal-based catalyst. The elastomer may be silicone rubber or the elastomer may be polyurethane. The catalyst may be platinum-based. In accordance with further related embodiments, the hydrophilic segment may include a hydrogel or the hydrophilic segment may include a hydrogel and an elastomer.

In accordance with another embodiment of the invention, a method for forming a cochlear implant electrode includes preparing a hydrophilic segment and placing the hydrophilic segment in a first section of an electrode mold. Electrical contacts are placed in a second section of the electrode mold and an elastomeric carrier is injected into the mold. In accordance with related embodiments, preparing a hydrophilic segment may include forming a hydrogel. Similarly, preparing a hydrophilic segment may include mixing a hydrogel and an elastomer. In addition, mixing a hydrogel and an elastomer may include mixing a hydrogel and liquid silicone rubber. In accordance with other related embodiments preparing a hydrophilic segment may include mixing an elastomer and a metal-based catalyst, and mixing an elastomer and a metal-based catalyst may include mixing liquid silicone rubber and a platinum-based catalyst.

In accordance with a further embodiment of the invention, a method for preparing a hydrophilic segment includes adding a metal-based catalyst to an elastomer and mechanically mixing the metal-based catalyst and the elastomer to form a cross-linked product. The mixture is de-gassed and cured in a segment mold. The mixture is then immersed in a polymerization solution and suspended in a sealed glass reactor. In accordance with related embodiments, the method may also include raising the temperature to allow a monomer, initiator, and cross-linker to react and removing monomers and unreacted hompolymers by soxlet extraction in distilled water.

BRIEF DESCRIPTION OF THE DRAWINGS

The features of the invention will be more readily understood by reference to the following detailed description, taken with reference to the accompanying drawings, in which:

FIG. 2 is a pictorial illustration of the electrode of FIG. 1;

FIG. 3 is a pictorial illustration of the electrode of FIG. 2 showing initial swelling of the hydrophilic segment;

FIG. 3A is a pictorial illustration of the electrode of FIG. 3 showing a portion of the hydrophilic segment and the electrode carrier detached from one another;

DETAILED DESCRIPTION OF SPECIFIC EMBODIMENTS

The present application pertains to the formation of implantable apparatuses such as pacemakers, cochlear implants, and other nerve stimulating devices. In accordance with the invention, polydimethylsiloxane (PDMS)-based elastomers are used to aid in the positioning of the implantable device subsequent to insertion into the body of a subject or patient.

Modeling of intra-cochlear stimulation and animal EABR data indicates that an electrode (or electrode array) positioned close to the inner wall of the scala tympani would be beneficial to the neuro-stimulation of cochlea implants (hence the name perimodiolar electrode). There is a consensus that such a perimodiolar electrode would lower psyco-accoustic threshold, increase the dynamic range of stimulation, and reduce channel interaction. Other potential benefits expected from a perimodiolar electrode array include reduced power consumption to drive the implant, reduced side effects for the subject or patient, implementation of innovative stimulation schema, and better place coding of frequency. Further, a perimodiolar electrode would allow a larger number of electrodes to be used effectively. It is hoped that an increase in the control of place stimulation would contribute toward raising the level of subjects or patients with poor hearing performance. An additional, potential benefit expected from a perimodiolar electrode is the side effect of unwanted and unnecessary stimulation would be reduced (especially reduced facial nerve stimulation).

Figure 1:
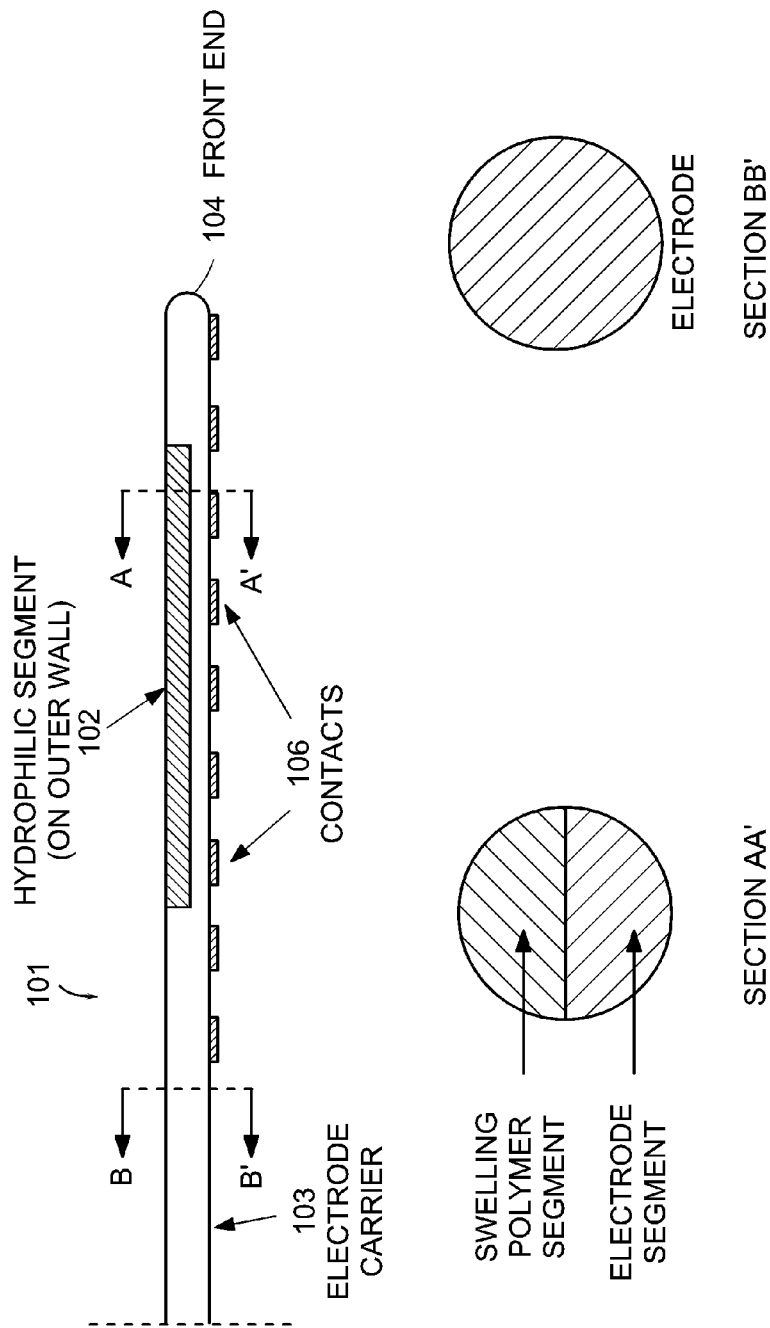
FIG. 1 is a graphical illustration of an electrode with a hydrophylic segment prior to insertion into a cochlea in accordance with one embodiment of the invention.
Figure 4:
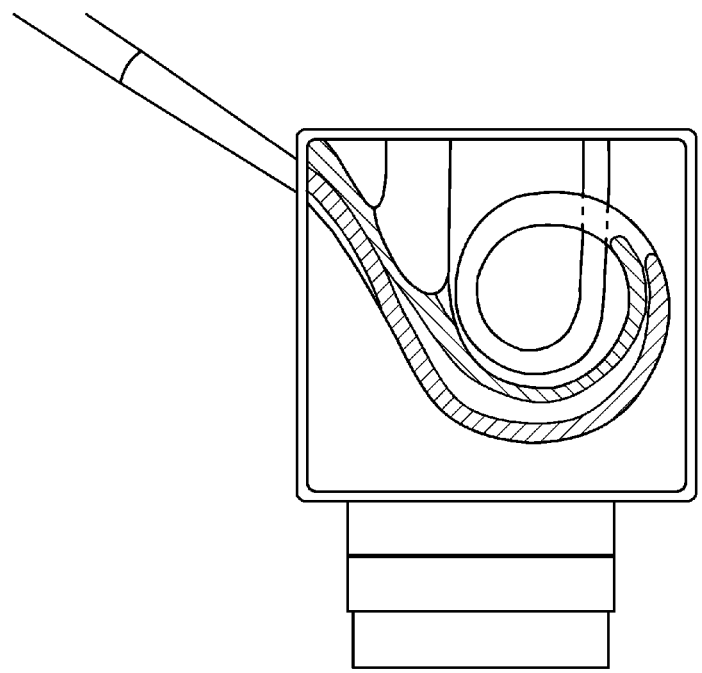
FIG. 4 is a pictorial illustration of an electrode in accordance with an embodiment of the invention after insertion in a scala tympani model.

FIGS. 1 and 2 illustrate a perimodiolar electrode with a hydrophylic segment prior to insertion into a cochlea in accordance with one embodiment of the invention. In accordance with this embodiment, the perimodiolar electrode 101 is designed for implantation into the cochlea of a subject and includes an electrode which can surround the modiolus or the inner wall (also called the medial wall) of the scala tympani. The electrode 101 includes a front end 104 and a back end 105. The electrode 101 also includes a hydrophilic segment 102 that is initially substantially fully connected to an electrode carrier 103. The cross sectional shape of the electrode 101 may be ellipsoid, round, somewhat rectangular, or any combination of the above. Similarly, the electrode 101 may be tapered or un-tapered along its length. When the hydrophilic segment 102 is substantially fully connected to the electrode carrier 103, the overall electrode 101 appears as a single unit, as shown in cross section A-A' of FIG. 1. When the electrode 101 is fully or partially introduced in the scala tympani spiral, it lays against the outer wall of the lumen.

Figure 5:
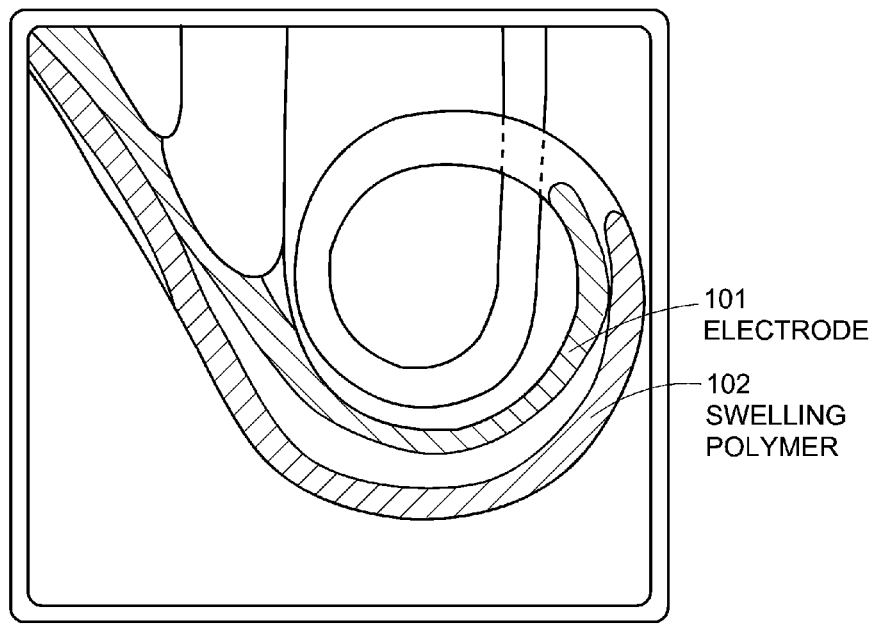
FIG. 5 is a pictorial illustration of the electrode of FIG. 4 after the hydrophilic segment swells.

FIGS. 3 and 5 illustrate that at some time after insertion into the scala tympani, the hydrophilic segment 102 of the electrode 101 begins swelling. The swelling of the hydrophilic polymer causes an increase in diameter as well as an elongation of the hydrophilic segment 102. Eventually, the swelling hydrophilic segment 102 detaches itself from the electrode carrier 103, except at the front end 104 and back end 105, as shown in FIGS. 3 and 5. The swelling segment of the electrode stays in close contact with the outer wall of the scala tympani. Elongation of the hydrophilic segment 102 causes the electrode 101 to position itself against the inner wall of the scala tympani as shown in FIG. 5.

The shape of the swelling hydrophilic segment 102 is determined by the mold that receives the injection of the polymer or other composition from which the segment it is formed. The shape may be that of a half circle, an ellipsoid, a rectangle, or any other shape which may promote or restrict the swelling properties of the segment in relation to the electrode carrier. The increase in volume of the swelling polymer is a control parameter and may vary between 10% and 60% depending on the hydrophilic mixture. The elongation of the swelling polymer may be anywhere between 10% and 50%. The relative size of the swelling polymer compared to the electrode carrier may be arbitrary.

In its final state, the electrode 101 consists of two connected branches and as shown in FIG. 3. The electrode carrier 103 and the hydrophilic segment 102 both have a front-end connection 301 and a back-end connection 302. The front-end connection 301 and back-end connection 302 consist of any means which keeps the electrode carrier 103 and the hydrophilic segment 102 connected before, during, and after completion of swelling while permitting detachment of the hydrophilic segment 102 over at least part of the distance between the front-end connection 301 and the back-end connection 302. Such a connection includes but is not limited to polymer bonding, clip, pin-notch system, or any means as deemed profitable.

In the embodiments described herein, the front-end connection 301 is dis-connectable for the purpose of ex-plantation of the electrode 101 when necessary. Thus, when the implant needs replacement, the hydrophilic segment 102 is easily dis-connectable. In order to achieve dis-connectibility, the hydrophilic segment 102 and the electrode carrier 103 may be joined by a bare PtIr ribbon section 107, which comes out of the hydrophilic segment 102 and is lodged snuggly or loosely in an oriented silicone cavity 108 molded on the electrode carrier 103. In case of revision surgery, the hydrophilic segment 102 can be dislocated at the front-end connection 301 by simply pulling back on the hydrophilic segment 102 with sufficient force. FIG. 3A shows the hydrophilic segment 102 and the electrode carrier 103 disconnected from one another. The front-end connection 301 may be any other system known in the art and deemed advantageous. The back-end connection 302 may be accomplished through polymer bonding. Similarly, the back-end connection 302 may be accomplished through a medical grade titanium clip 109 such as those produced by Heinz Kurz GmbH in Dusslingen, Germany. The branches may also be attached with a PtIr wire, a silicone ring, or surgical sutures.

As can be seen in FIGS. 1, 2 and 3, the front end 104 generally projects beyond the hydrophilic segment 102 by some distance. However, the length ratio between the front end 104 and hydrophilic segment 102 may be anywhere from 0.3 to 3. The electrode carrier 103 usually includes a single row of contacts 106 facing the modiolus and the number of contacts 106 may be arbitrarily fixed. Further, the electrode 101 may have double or more contacts to increase the surface area of the electrode and reduce the impedance. The contact distribution between the front end 104 and the rest of the electrode 101 can be arbitrary. For an n contacts electrode, the front end 104 may receive anywhere from 0.1n to 0.8n of the contacts, as deemed advantageous for stimulation. It may also be that the electrode 101 is built with no front end 104 and that the hydrophilic segment 102 converges at the tip of the electrode 101. In addition, the contact spacing on the front end 104 may be equal, logarithmic, or equal and logarithmic. Dummy contacts or markers can be placed between the last contact on the electrode (most basal) and for a distance of up to 15 mm. Dummy contact or marker separation is arbitrary. The role of the dummy contact or marker is to give an indication of the insertion depth of the electrode to the surgeon. The dummy contact or marker may be shape coded to indicate distance along the array without having to count the number of interval between the contacts.

Figure 6:
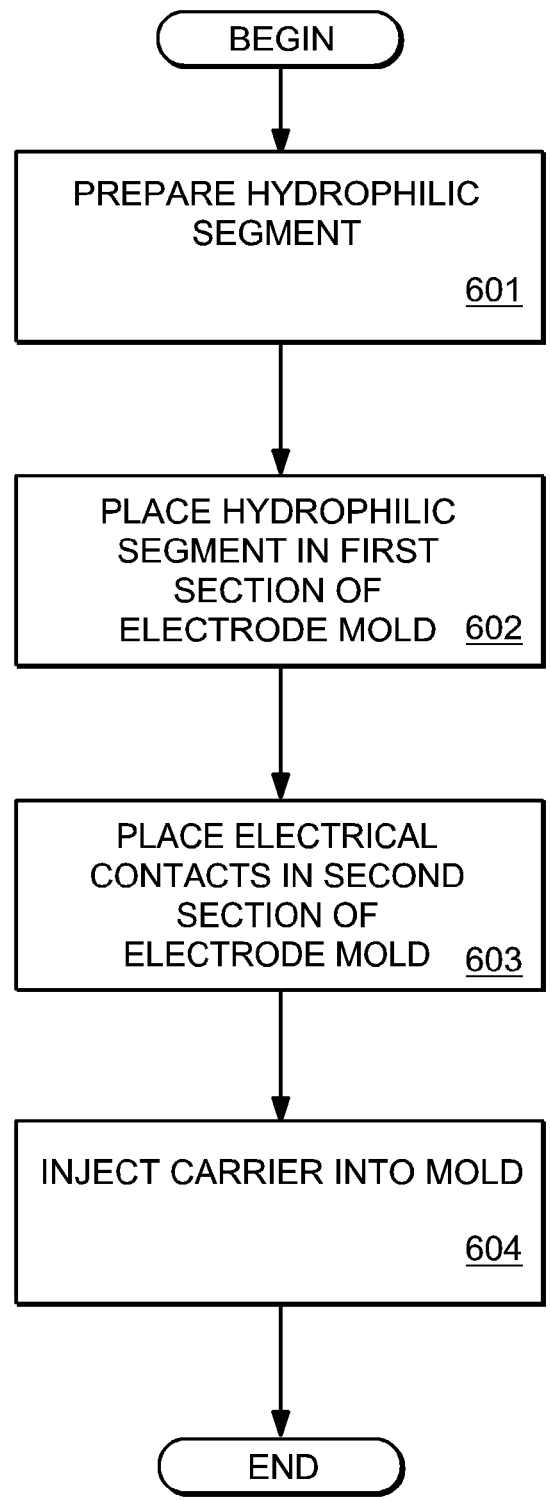
FIG. 6 is a flow chart illustrating a method for making a perimodiolar electrode in accordance with another embodiment of the invention.

FIG. 6 is a flow chart illustrating a method for making a perimodiolar electrode in accordance with another embodiment of the invention. In process 601 a hydrophilic segment is prepared and then placed 602 in a first section of an electrode mold. Preparing a hydrophilic segment may include forming a hydrogel. (For purposes of the present application, the term "hydrogel" refers to a coherent three-dimensional polymeric network that can imbibe large quantities of water without the dissolution of the polymer network.) Preparing a hydrophilic segment may further include a mixing a hydrogel and an elastomer. In addition, mixing a hydrogel and an elastomer may include mixing a hydrogel and liquid silicone rubber. Similarly, preparing a hydrophilic segment may include mixing an elastomer and a metal-based catalyst, and mixing an elastomer and a metal-based catalyst may include mixing liquid silicone rubber and a platinum-based catalyst. Electrical contacts are placed 603 in a second section of the electrode mold and an elastomeric carrier is injected 604 into the mold.

As discussed above, the hydrophilic segment can be prepared from a hydrogel or a multi-component system of hydrogel and elastomer (silicone rubber or polyurethane). The multi-component system may be fabricated by co-polymerization, grafting, blending, simultaneous interpenetrating polymer network, and sequential interpenetrating polymer network. An interpenetrating polymer network ("IPN") is defined as an intimate combination of two or more polymers, at least one of which is synthesized or cross-linked in the immediate presence of the other. The cross linking of at least one of the polymer systems distinguishes an IPN from an ordinary blend or a co-polymer.

Figure 7:
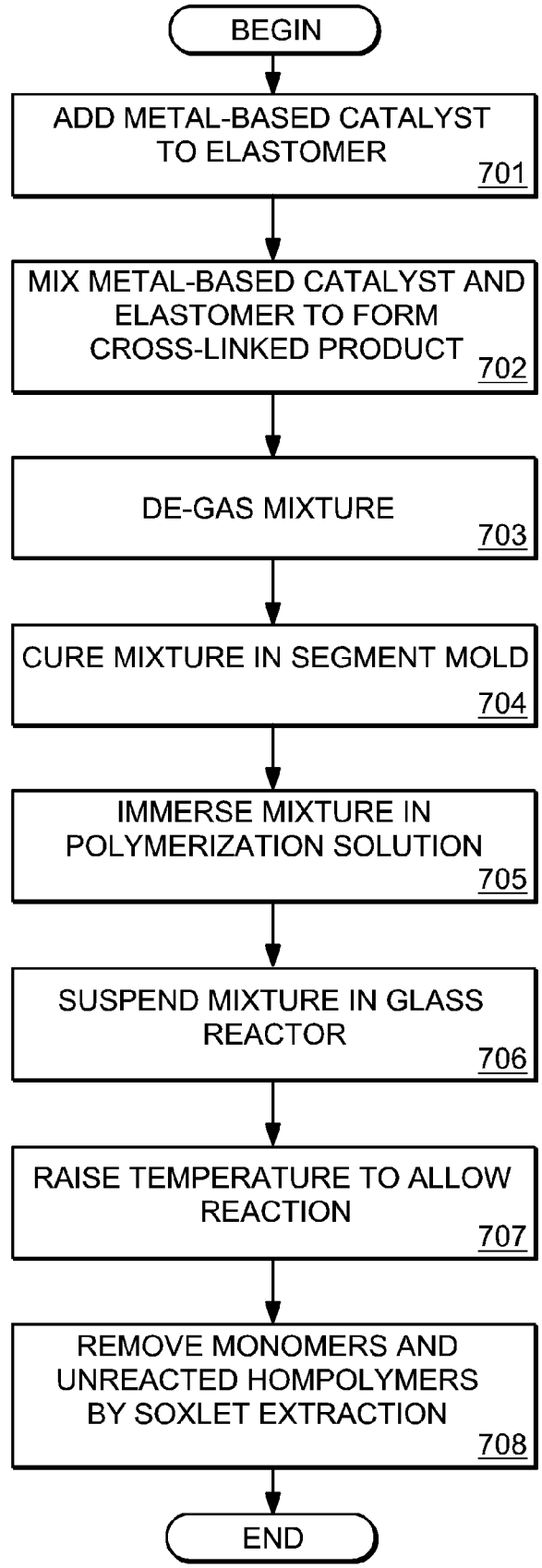
FIG. 7 is a flow chart illustrating a method for making a hydrophilic segment in accordance with a further embodiment of the invention.

FIG. 7 is a flow chart illustrating a method for making a hydrophilic segment in accordance with a further embodiment of the invention. In accordance with this embodiment, the hydrophilic segment is prepared by adding, in process 701, a metal-based catalyst to an elastomer. For example, liquid silicone rubber ("LSR") may be mixed with a platinum-based catalyst. The metal-based catalyst and the elastomer are mechanically mixed 702 to form a cross-linked product. The mixture is de-gassed in process 703 and injected into a mold with a pre-designed cavity shaped for the hydrophilic segment. After a curing (and optionally, post-curing) the mixture in the segment mold in process 704, the product is immersed 705 for approximately twenty-four hours at room temperature in a polymerization solution that may include acrylic acid or acrylamide monomer. The swollen hydrophilic segment samples are suspended 706 in a sealed glass reactor. The temperature is raised 707 and kept at a definite temperature to allow the monomer, initiator, and cross-linker to react. The monomers and unreacted hompolymers are removed 708 by soxlet extraction in distilled water. As described above with respect to the embodiment of FIG. 6, the hydrophilic segment is placed in a first part of a mold, and, after fixation of wires inside a second part of the mold, LSR is injected in to the mold to produce the final electrode.

There are several advantages of the design disclosed in the present application over prior art: a) the electrode carrier and hydrophilic polymer are and remain attached during the insertion process; b) a surgeon does not have to perform any additional positioning since the electrode is self positioning post operatively; c) the connection to the electrode modiolus is independent of morphology; d) the front end of the electrode has less of a tendency to perforate the basilar membrane during the positioning process; e) no special tools are needed for insertion or positioning; f) the electrode and the insertion aperture on the bony promontory may remain small in diameter; and g) a section of the electrode (e.g., the front end) may be deeply inserted in the cochlear.

While the invention has been described in connection with specific embodiments thereof, it will be understood that it is capable of further modification. This application is intended to cover any variation, uses, or adaptations of the invention and including such departures from the present disclosure as come within known or customary practice in the art to which invention pertains.

What is claimed is:

1. A method for forming a cochlear implant electrode, the method comprising:
    preparing a hydrophilic segment, the hydrophilic segment having a wire that protrudes from one end of the hydrophilic segment;
    placing the hydrophilic segment in a first section of an electrode mold;
    placing electrical contacts in a second section of the electrode mold; and
    injecting an elastomeric carrier into the mold to produce the electrode, the electrode including an electrode carrier and the hydrophilic segment, and to form a cavity in the electrode carrier, the cavity configured to releasably hold the wire, whereby the wire is easily disconnectable from the cavity when sufficient force is applied to the wire.

2. A method according to claim 1, wherein preparing a hydrophilic segment includes forming a hydrogel.

3. A method according to claim 1, wherein preparing a hydrophilic segment includes mixing a hydrogel and an elastomer.

4. A method according to claim 3, wherein mixing a hydrogel and an elastomer includes mixing a hydrogel and liquid silicone rubber.

5. A method according to claim 1, wherein preparing a hydrophilic segment includes mixing an elastomer and a metal-based catalyst.

6. A method according to claim 5, wherein mixing an elastomer and a metal-based catalyst includes mixing liquid silicone rubber and a platinum-based catalyst.

7. A method according to claim 1, wherein preparing a hydrophilic segment includes:
    adding a metal-based catalyst to an elastomer;
    mechanically mixing the metal-based catalyst and the elastomer to form a crossed-linked product mixture;
    de-gasing the mixture;
    curing the mixture in a segment mold to form a product;
    immersing the product in a polymerization solution; and
    suspending the product in a sealed glass reactor.

8. A method according to claim 7, further comprising:
    raising the temperature to allow portions of the product and the polymerization solution to react; and
    removing monomers and unreacted hompolymers by soxlet extraction in distilled water.

9. A method according to claim 1, further comprising:
    placing a clip around the elastomeric carrier near at least one end of the first section.

10. A method according to claim 1, wherein the wire comprises a platinum iridium ribbon wire.

11. A method for producing a cochlear implant electrode, the method comprising:
    providing a hydrophilic segment having a wire that protrudes from one end of the hydrophilic segment; and
    forming an electrode carrier connected to the hydrophilic segment at a front-end and a back-end connection, the electrode carrier having one or more electrical contacts and a cavity on the electrode carrier near the front-end connection, the cavity configured to releasably hold the wire, whereby the hydrophilic segment is easily disconnectable from the electrode carrier at the front-end connection when sufficient force is applied to the wire.

* * * * *